United States Patent
Goto et al.

(10) Patent No.: US 7,366,277 B2
(45) Date of Patent: Apr. 29, 2008

(54) TOMOGRAPHIC DEVICE AND METHOD THEREFOR

(75) Inventors: Taiga Goto, Kashiwa (JP); Osamu Miyazaki, Moriya (JP); Koichi Hirokawa, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 10/587,128

(22) PCT Filed: Jan. 20, 2005

(86) PCT No.: PCT/JP2005/000697

§ 371 (c)(1),
(2), (4) Date: Jul. 21, 2006

(87) PCT Pub. No.: WO2005/072612

PCT Pub. Date: Aug. 11, 2005

(65) Prior Publication Data
US 2007/0165769 A1      Jul. 19, 2007

(30) Foreign Application Priority Data
Feb. 2, 2004    (JP) .............................. 2004-026145

(51) Int. Cl.
*H05G 1/60*     (2006.01)

(52) U.S. Cl. .............................. 378/4; 378/4; 378/210; 378/901

(58) Field of Classification Search ............ 378/4, 378/210, 901
See application file for complete search history.

(56) References Cited

U.S. PATENT DOCUMENTS

| | | | | |
|---|---|---|---|---|
| 5,838,756 A | * | 11/1998 | Taguchi et al. ................ | 378/4 |
| 6,307,909 B1 | * | 10/2001 | Flohr et al. .................... | 378/4 |
| 6,765,983 B2 | * | 7/2004 | Yan et al. ....................... | 378/8 |
| 7,006,593 B2 | * | 2/2006 | Kokubun et al. .............. | 378/8 |
| 7,212,602 B2 | * | 5/2007 | Tsujii ............................. | 378/8 |
| 2003/0016791 A1 | * | 1/2003 | Ukita .......................... | 378/210 |
| 2005/0094760 A1 | * | 5/2005 | Hagiwara ....................... | 378/4 |

FOREIGN PATENT DOCUMENTS

| | | |
|---|---|---|
| JP | 10-80419 | 3/1998 |
| JP | 2003-24326 | 1/2003 |

* cited by examiner

*Primary Examiner*—Courtney Thomas
*Assistant Examiner*—Alexander H Taningco
(74) *Attorney, Agent, or Firm*—Cooper & Dunham, LLP

(57) ABSTRACT

An image reconstruction area of a subject is divided into a plurality of image data segments, among projection data obtained by projection, projection data segments necessary for back projection processing are cut out for every image data segments and back projection processing is performed for every image data segments by making use of the cut out projection data segments. Further, detector addresses of the projection data to be used for the back projection processing are obtained from a plurality of limited number of detector addresses within the concerned image data segment region. As a result, a device is realized which permits to produce a high quality tomographic image with high speed by using a small amount of a high speed memory.

14 Claims, 8 Drawing Sheets

(A)

Single Row Detector Type CT (B)

Multi Row Detector Type CT

TOMOGRAPHIC DEVICE AND METHOD THEREFOR

FIELD OF THE INVENTION

The present invention relates to a tomographic device and a method therefor, which produces highly accurate tomographic images of a subject from projection data obtained from a radioactive ray source and radioactive ray detector constituted movable relative to the subject in the circumferential revolving direction and in the body axis direction.

CONVENTIONAL ART

Recently, a multi detector row computer tomography (herein after will be called as MDCT) has appeared, in which a plurality of detector rows are arranged in the circumferential revolving axis direction. In comparison with a single detector row computer tomography (herein after will be called as SDCT), since the MDCT is provided with detectors in broad width by arranging a plurality of detector element rows along the circumferential revolving axis direction, a broad imaging area can be covered at one time. Further, with the MDCT, when the subject is moved relatively with further higher speed, the scanning time is shortened, thereby, artifacts due to body motion such as breathing can be reduced and a resolution in the circumferential revolving axis direction can be significantly enhanced. FIG. 1 is diagrams showing fundamental constitutional differences between the SDCT and MDCT. The SDCT is provided with X-ray detectors 11 in a single row with respect to a single X-ray source 10 as shown in FIG. 1 (A), and the MDCT is provided with X-ray detectors 12 in a plurality of rows (in the drawing, 8 rows) with respect to a single X-ray source 10 as shown in FIG. 1 (B).

In the case of MDCT, since every X-ray detector rows locate in different slanting angles with respect to the circumferential revolving axis direction, parameters for specifying the projection data increase such as channel, row and slanting angle and now the image reconstruction methods therefor are complicated and diversified. Under this circumstance, a variety of image reconstruction algorithms are proposed such as 3-dimensional Radon transformation method and 3-dimensional back projection method (3-dimensional reconstruction methods) as a reconstruction algorithm when a further accuracy is required, and including weighted back projection method for helical correction (2-dimensional reconstruction method) used for MDCT requiring high speed computation, which is formulated by improving a weighted back projection method for helical correction being used for the for the SDCT.

Among these image reconstruction methods, in the weighted back projection method for helical correction, which is a 2-dimensional image reconstruction method, the reconstruction time per one tomographic image is short in that from a few seconds to a few tens seconds. In an actual device, when a dedicated hardware such as DSP board and ASIC is used, the images can be reconstructed in about 0.2~0.5 seconds per one tomographic image. Further, an amount of memory required for producing projection data equivalent to one row detectors from plural row detectors and for performing the 2-dimensional back projection is almost the same as required in the SDCT and is fully satisfactory in view of the cost thereof. Accordingly, in MDCTs provided with detector rows such as 2 rows and 4 rows, the improved 2-dimensional reconstruction method is generally employed.

However, since the weighted back projection method for helical correction uses an algorithm which neglects beam slanting (cone angle) of X-rays in the circumferential revolving direction, an image quality of MDCTs with detectors of more than 16 rows is significantly deteriorated due to the influence of the cone angle, which reduces the diagnostic accuracy of tomographic devices. For this reason, the application of the weighted back projection method for helical correction is limited to MDCTs with detectors of about 2~8 rows of which influence of cone angle is comparatively small.

Recently, since the number of rows of the detectors increases, image reconstruction methods with high accuracy for MDCTs having a broad cone angle have been generally studied. Among these, although 3-dimensional Radon transformation method is a precise image reconstruction method, an extremely long computing time such as from a few tens minutes to a few hours for obtaining one slice image is required, which prevents practical use thereof.

On the other hand, although 3-dimensional back projection method is an approximal image reconstruction method, however, is an image reconstruction method with comparatively high accuracy which takes into account of the cone angle, of which computation time for one slice image is about from a few minutes to a few tens minutes, and when a dedicated hardware is used, the computation time will be further shortened, therefore, the method performs a comparatively high speed computation and practical. For this reason development of realizing an MDCT implementing the 3-dimensional back projection method is being advanced.

One of the problems of the image reconstruction method with the highly accurate 3-dimensional back projection method correctly taking into account of the cone angle is to increase significantly the memory amount required when performing the image reconstruction computation in comparison with the 2-dimensional back projection method used for the conventional SDCTs. Namely, in the back projection computing unit therein, data (projection data) required for the back projection are read out from the hard disk, store the same in a high speed memory (for example, a cache memory) and the back projection processing is executed with the data in the high speed memory. In this instance, when the amount of data to be processed is large, a part of the data are stored in a low speed large capacity memory (for example, DRAM), and when data necessary for the computation do not exist in the high speed memory, the data are successively read out from the low speed memory, the data in the high speed memory are renewed and after the renewing, the processing is performed. Since the high speed memory is generally expensive, the capacity of the high speed memory is mostly small in comparison with that of the inexpensive low speed memory.

Now, the amount of memory (amount of data to be processed) required for the back projection processing is discussed, in the weighted back projection method for helical correction using the 2-dimensional back projection method, helical correction projection data for one detector row are produced from a plurality of data through interpolation. Since the back projection processing is performed for every view, the necessary amount of memory (amount of data to be processed) is that for one view. Namely, the amount of memory necessary for one time (for one view) back projection is that for one row × that for number of channels. For example, when assuming that the number of channels is 1000 [ch], the necessary amount of memory is about 2 [Kbyte] (=1000 [ch]×1 [row]×2 [byte]). On the other hand, in the 3-dimensional Radon transformation method and the 3-dimensional back projection method, since the detector data from a plurality of rows have to be treated as they are, the amount of memory necessary for one time (for one view) back projection processing increases in proportion to the number of detector rows. For example, in the case of MDCT having detectors of 128 rows, the amount of memory necessary for the weighted back projection method for helical correction is 128 times in that about 256 [Kbyte].

As indicated above, since the necessary amount of memory (amount of data to be processed) increases and the data can not be stored in the high speed memory within the processing unit, a memory swapping is required in such a manner that the data to be processed are temporarily stored in a low speed memory connected outside of the processing unit and the processing is performed while successively replacing data depending on the necessity. In this instance, the processing speed depends on the data transmission speed between the high speed memory and the low speed memory and a processing speed more than the data transmission speed can not be obtained, which causes a delay of the processing time. Further, even when a dedicated hardware is prepared, like delay depending on the data transmission speed is caused. As will be understood from the above, in order to obtain a processing speed more than the data transmission speed, the capacity of the expensive high speed memory has to be increased, however, which significantly increases the cost thereof and is not desirable.

Another problem of the image reconstruction method with the highly accurate 3-dimensional back projection method correctly dealing the cone angle is to increase the processing time in comparison with the 2-dimensional back projection method used for the conventional SDCTs. In the 2-dimensional back projection method used for such as SDCTs and MDCTs with 4 detector rows, since the back projection is performed by using scanning data on an imaginary circular orbit of a single detector row which are obtained by helically correcting scanning data on a helical orbit by weighting, the address calculation of the detectors in the row direction was not necessary. On the other hand, in the 3-dimensional back projection method, in order to access detector data in a plurality of rows, calculation of detector address (addressing) in the channel direction and in the row direction is required through complicating computation according to, for example, the following equations. Further, the processing equations for the addressing applied to the 3-dimensional back projection method according to the present invention are not limited to the following equations (1)~(6), but a variety of processing equations can be applied therefor.

$$t_1(x_1, y_1, \phi) = x_1 \cdot \cos\phi + y_1 \cdot \sin\phi \quad (1)$$

$$v_1(x_1, y_1, z_1, \phi) = \frac{(z_1 - z_s(x_1, y_1, \phi)) \cdot SID}{L(x_1, y_1, \phi)} \quad (2)$$

$$z_s(x_1, y_1, \phi) = \frac{T \cdot \left[\phi + \arcsin\left\{\frac{t_1(x_1, y_1, \phi)}{SOD}\right\}\right]}{2\pi} + z_{so} \quad (3)$$

$$L(x_1, y_1, \phi) = D(x_1, y_1, \phi) + w_1(x_1, y_1, \phi) \quad (4)$$

$$D(x_1, y_1, \phi) = \sqrt{SOD^2 - t_1^2} \quad (5)$$

$$w_1(x_1, y_1, \phi) = -x_1 \cdot \sin\phi + y_1 \cdot \cos\phi \quad (6)$$

Herein, $x_1, y_1, z_1$ shows a coordinate position of voxsel 1 in an image reconstruction area, $\phi$ shows a circumferential revolving position of parallel beams, w, t, v are coordinate axes of the detectors wherein w represents an axis in advancing direction of the parallel beams, t represents an axis in perpendicular direction (the channel direction of the parallel beams) to the advancing direction and v represents an axis of the detectors in the circumferential revolving axis direction. $w_1, t_1, v_1$ represents a coordinate position on the w, t, v axes when parallel beams in $\phi$ phase pass the coordinate position $(x_1, y_1)$. SID represents the distance between the radioactive ray source and the detectors and SOD represents the distance between the radioactive ray source and the center of rotation. $z_s$ represents the position of the radioactive ray source in z axis direction and $z_{so}$ represents the position $z_s$ when the circumferential revolving phase of the radioactive ray source is zero.

FIG. 2 is a diagram for explaining the general idea of image reconstruction method in SDCT. FIG. 3 is a diagram for explaining the general idea of image reconstruction method in MDCT. In the computation with the image reconstruction method for the MDCT as shown in FIG. 3, the addresses of reconstructed image 30 in x and y directions vary linearly in the channel direction and non-linearly in the row direction. On the other hand, in the computation with the image reconstruction method for the SDCT as shown in FIG. 2, in response to the linear address change of reconstructed image 20 in x and y directions, the corresponding detector addresses change linearly in the channel direction. As will be understood from the above, the 3-dimensional back projection method shows a drawback of accompanying a significant delay for processing data required for the back projection computation due to 2-dimensional addressing and complex addressing. In particular, the addressing in the row direction in the 3-dimensional back projection method requires to use extremely complicated non-linear functions and simplification by modifying the functions are difficult, which is the great cause of the data processing delay.

A tomographic device which takes into an account of resolving such problems is, for example, disclosed in JP-A-2003-24326, in which back projection computation (tomographic image reconstruction calculation) for performing back projection on 2-dimensional or 3-dimensional tomographic image reconstruction area imaginarily set on a region of interest of a subject is performed by a computer for every divided region formed by dividing the tomographic image reconstruction area, thereby, the tomographic image reconstruction calculation can be performed orderly for every optimum region (the divided region) determined in view of the cache memory size, as a result, data reuse rate in the cache memory is increased, data access times with the memory is reduced, total data transference time for the tomographic image reconstruction is shortened and the tomographic image reconstruction calculation time is shortened.

However, as disclosed in JP-A-2003-24326, in order to perform back projection on the divided tomographic image reconstruction region stored in the high speed cache memory, all of the projection data thereof are stored in the cache memory, which increases the amount of high speed memory and is not preferable in view of the cost of the device. Further, in the case of MDCTs of which increase in number of detector rows is extreme, the amount of data to be processed becomes significant, which causes significant increase of the high speed memory amount and prevents processing cost reduction and high speed processing.

An object of the present invention is to provide a tomographic device and a method therefor which suppress capacity increase of a high speed memory, prevent significant increase of processing cost and permit to produce high quality tomographic images in high speed.

SUMMARY OF THE INVENTION

One feature of a tomographic device according to the present invention, which detects penetration light penetrated through a subject with a detection means arranged in 2-dimension and produces 3-dimensional tomographic image of a region of interest of the subject from the detected projection data, is to provide processing means which divides an image reconstruction area of the subject into a plurality of image data segment regions, extracts among the projection data detected by the detection means a projection data segment region necessary for back projecting on the image data segment region and performs 3-dimensional back projection computing processing for every image data segment region by making use of the extracted projection data segment region.

The tomographic device according to the present invention is constituted in such a manner that in order to reduce a high speed memory amount necessary for the back projection processing the image reconstruction area is divided into a plurality of small regions (image data segment region), a minimum projection data segment region necessary for the back projection computation processing is extracted for every divided image data segment region among the projection data obtained from the imaging and the back projection computing processing is performed for every image data segment region of the small region by making use of the data of the extracted projection data segment region.

Further, in order to maximize the utilization of the capacity of the high speed memory, it is preferable that the size of the projection data in the view direction is determined depending on the capacity of the high speed memory which can be utilized during the image reconstruction processing. Further, in order to reduce the complexity of the image reconstruction processing, it is preferable, when dividing the image reconstruction area into image data segments, to divide the same into small segments having the same size. Still further, in order to reduce the amount of memory necessary for data processing at one time, it is preferable that the size of the projection data segment region in the view direction is to be determined one for a single view.

Another feature of the tomographic device according to the present invention is that in the tomographic device provided with the above mentioned feature, the processing means approximately calculates the addresses of the projection data to be back projected through an interpolation processing based on a plurality of representative addresses of detecting means in the image data segment region. In other words, in the back projection processing for every image data segment, the addresses of the detecting means on the extracted projection data segment are calculated through an interpolation by making use of the plurality of the limited representative addresses of the detecting means on the image data segment region. Thereby, the address calculation of the detector means in the back projection processing can be performed in high speed.

BEST MODES FOR CARRYING OUT THE INVENTION

Figure 4:
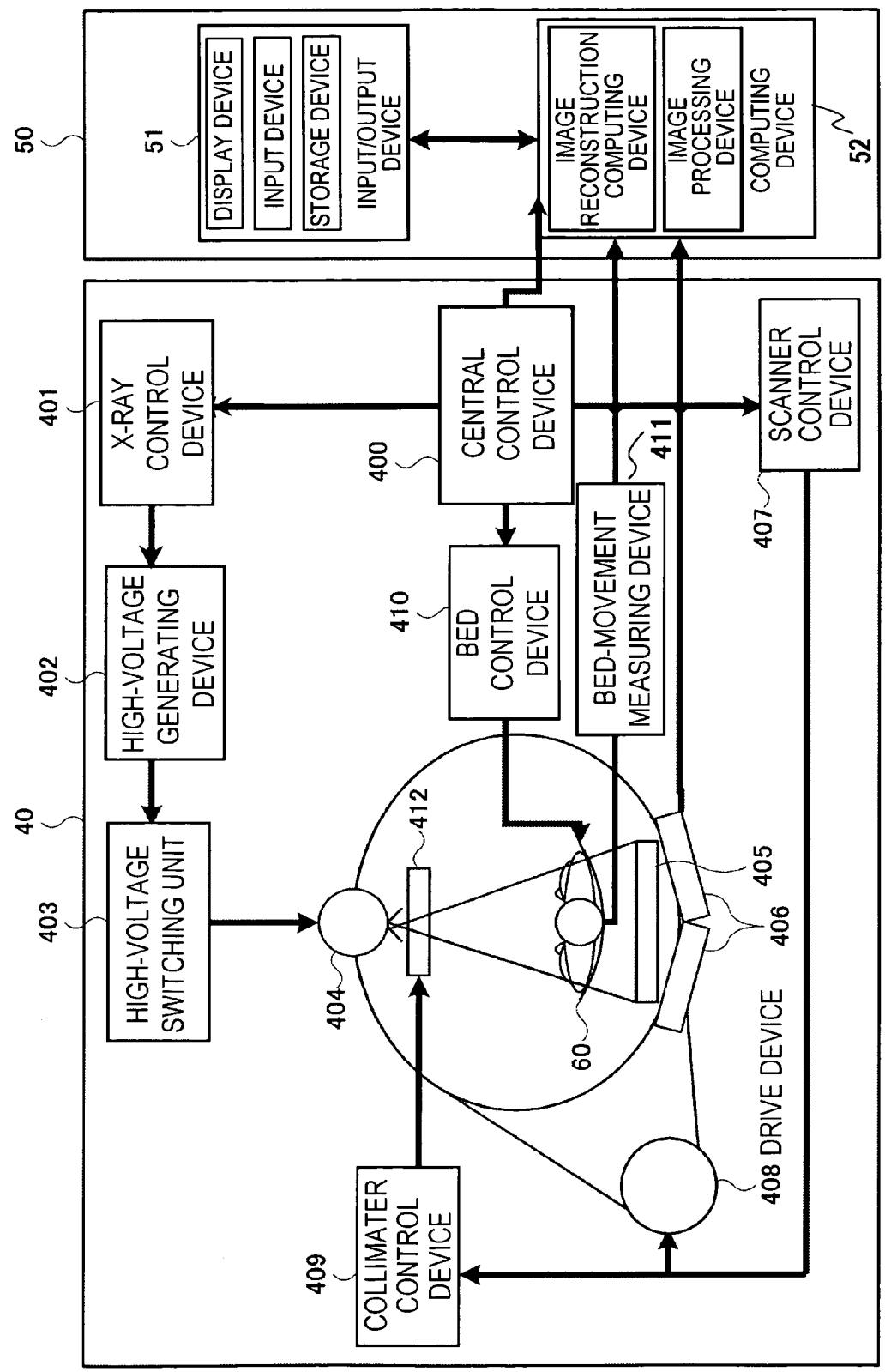
FIG. 4 is a diagram showing an entire constitution of an MDCT representing an embodiment of a tomographic device according to the present invention.

Herein below, an embodiment of the tomographic device according to the present invention will be explained in detail with reference to the drawings accompanied. FIG. 4 is a diagram showing an entire constitution of an MDCT representing an embodiment of a tomographic device according to the present invention. A scan method of the MDCT is a rotate-rotate method (the third generation) and the MDCT, when roughly sectioned, is constituted by a scanner 40, an operation unit 50 and a bed 60 for moving a subject while setting the same thereon.

The scanner 40 is constituted such as by a central control device 400, an X-ray control device 401, a high voltage generating device 402, a high voltage switching unit 403, an X-ray generating device 404, an X-ray detector 405, a pre-amplifier 406, a scanner control device 407, a scanner drive device 408, a collimator control device 409, a bed control device 410 and a bed movement measuring device 411. The operation unit 50 is constituted by an input-output device 51 including such as a display device, an input device and a memory device and a computing device 52 including such as an image reconstruction computing device and an image processing device. The input device is constituted by such as a mouse and a key board, and is for such as measuring bed moving speed information and an image reconstruction position and for inputting parameters of image reconstruction, the memory device is for storing these information and the display device is for displaying these information and a variety of data such as reconstructed images. The image reconstruction computing device is for processing projection data obtained from a multiple row detectors and the image processing device is for applying a variety of processing to the reconstructed images and for displaying the same.

The central control device 400 transmits control signals necessary for imaging to the X-ray control device 401, the bed control device 410 and the scanner control device 407, based on command inputs from the input device in the operation unit 50 with regard to such as scanning conditions (such as bed moving speed, X-ray tube current, X-ray tube voltage and slice position) and reconstruction parameters (such as a region of interest, reconstructed image size, back projection phase width and reconstruction filter function), and begins an imaging operation upon receipt of an imaging start signal. When the imaging operation begins, a control signal is sent to the high voltage generating device 402 from the X-ray control device 401, a high voltage is applied to the X-ray generating device 404 via the high voltage switching unit 403, X-rays emitted from the X-ray generating device 404 are irradiated to a subject and the penetrated light thereof makes incident to the X-ray detector 405. At the same time, from the scanner control device 407 a control signal is sent to the scanner drive device 408 and the X-ray generating device 404, the X-ray detector 405 and the pre-amplifier 406 are controlled so as to rotate circumferentially around the subject.

X-rays emitted from the X-ray generating device 404 are controlled of their irradiation area by a collimator 412 controlled by the collimator control device 409, absorbed (attenuated) by respective tissues within the subject, penetrate the subject and detected by the X-ray detector 405. The X-rays detected by the X-ray detector 405 are converted therein into an electric current and which is amplified by the pre-amplifier 406 and is input as projection data signals to the computing device 52 in the operation unit 50. The projection data signals input to the computing device 52 are subjected to an image reconstruction processing at the image reconstruction computing device in the computing device 52. The reconstructed image is stored at the memory device in the input-output device 51 and is displayed as a CT image on the display device in the input-output device 51.

Figure 1:
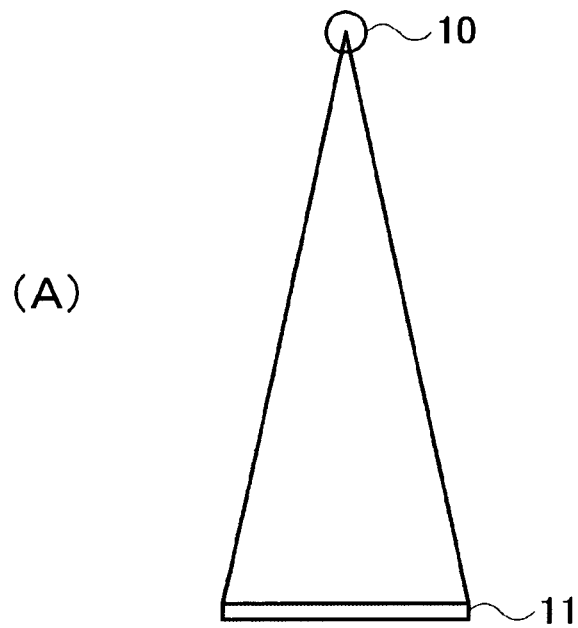
FIG. 1 is a diagram for explaining a fundamental constitutional difference between an SDCT and an MDCT.
Figure 1:
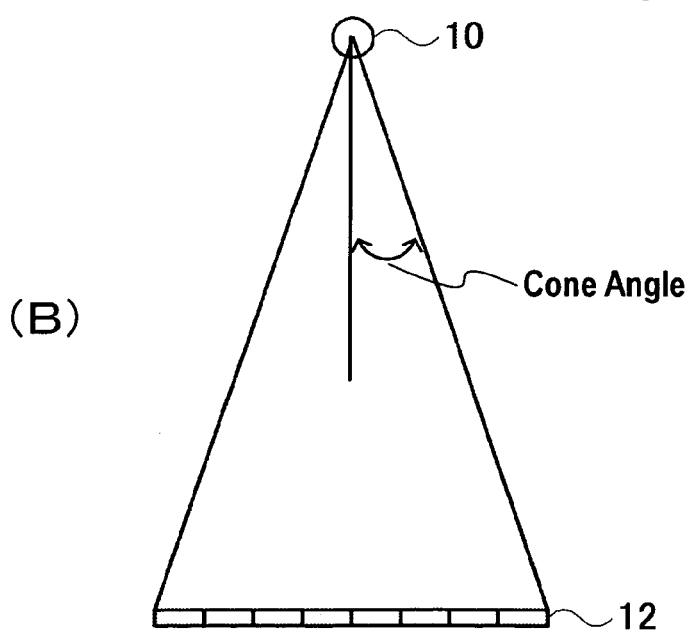
Figure 2:
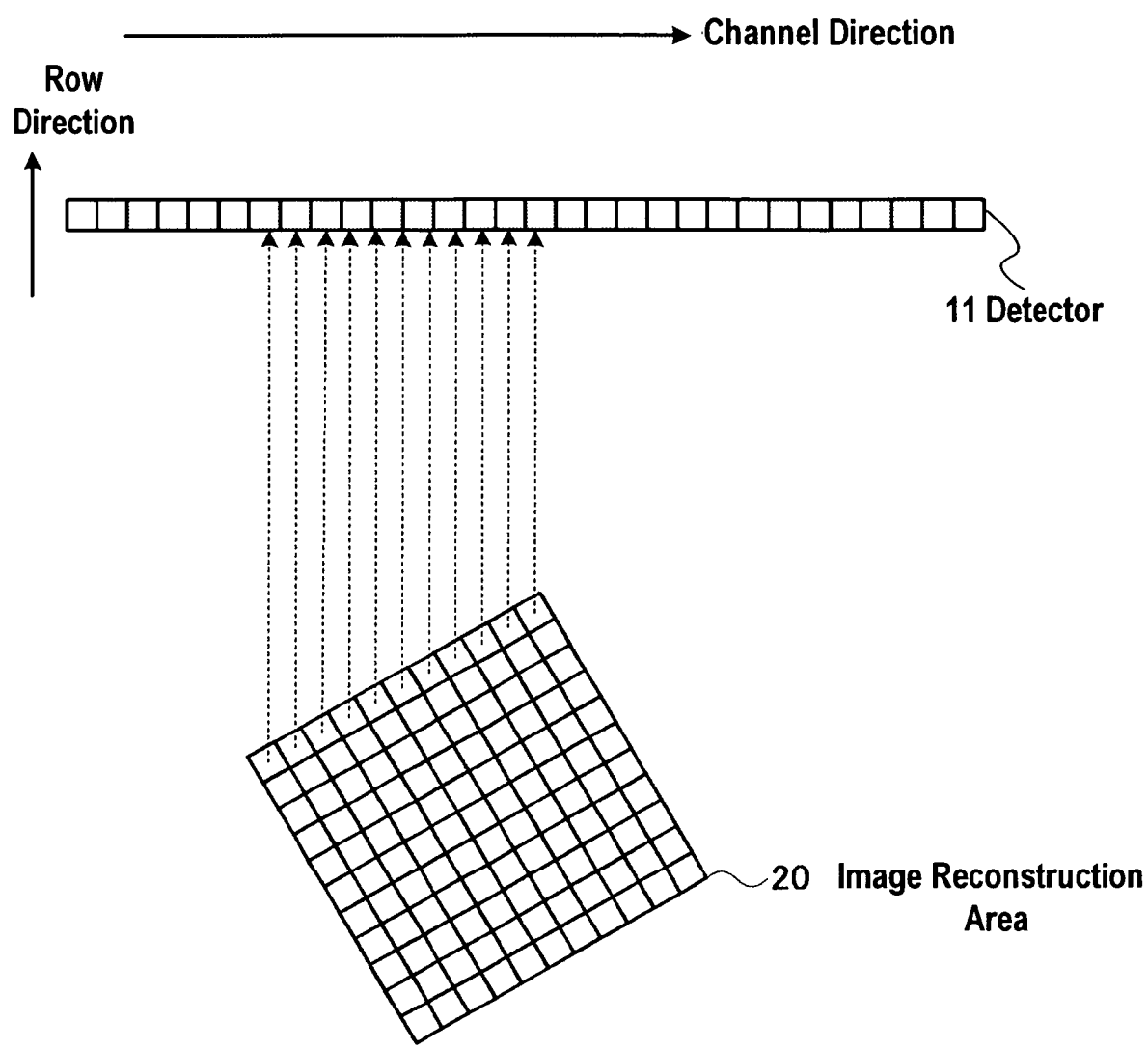
FIG. 2 is a diagram for explaining a general idea of the back projection image reconstruction method in the SDCT.
Figure 3:
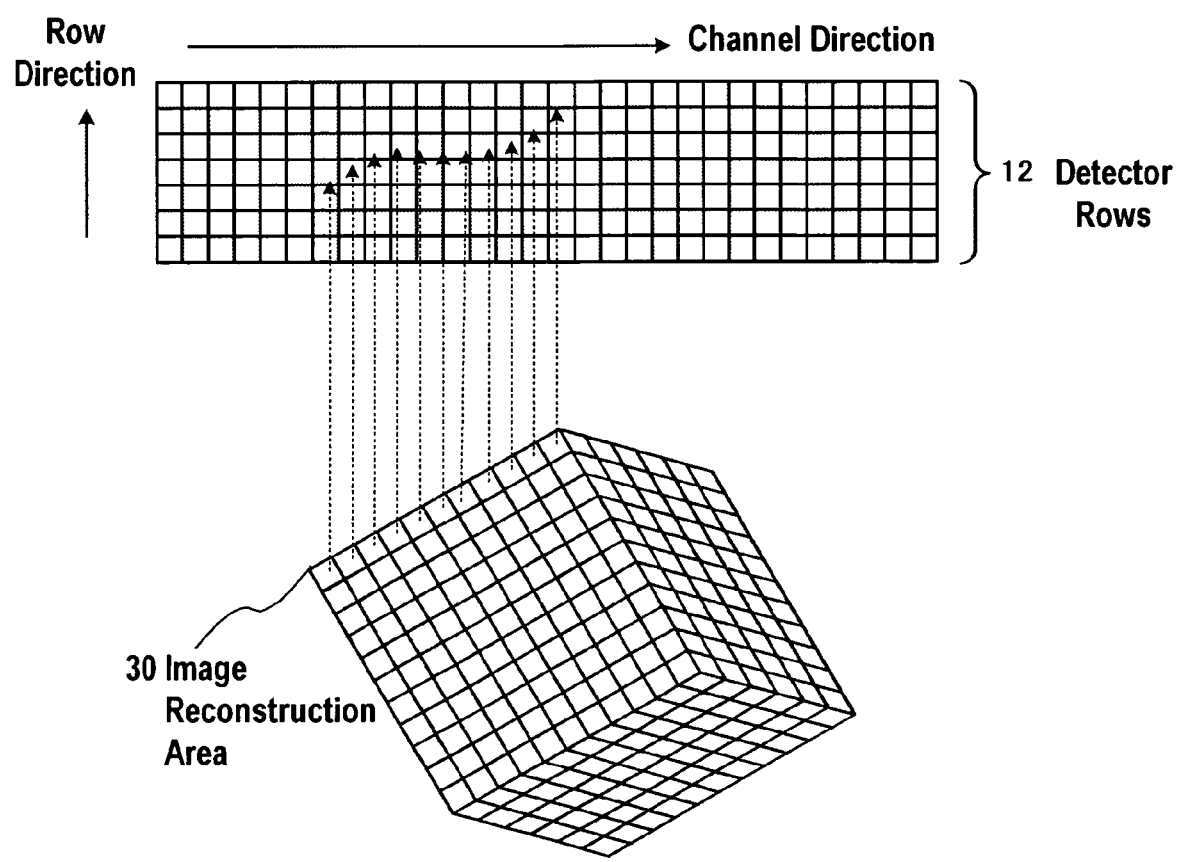
FIG. 3 is a diagram for explaining a general idea of the back projection image reconstruction method in the MDCT.

As shown in FIG. 1, different from the single row detector type CT, in the multiple row detector type CT, since detector elements are arranged in a plurality of rows in the circumferential revolving axis direction, as a whole, a detector having a broader width than the single row detector type CT is realized. Further, in the single row detector CT, the X-ray beams thereof cross perpendicularly to the circumferential revolving axis, on the other hand, in the multiple row detector type CT, the X-ray beams show slanting angles (cone angle) with respect to the circumferential revolving axis as the beams move away from the mid plane (center row) of the detector rows.

Figure 5:
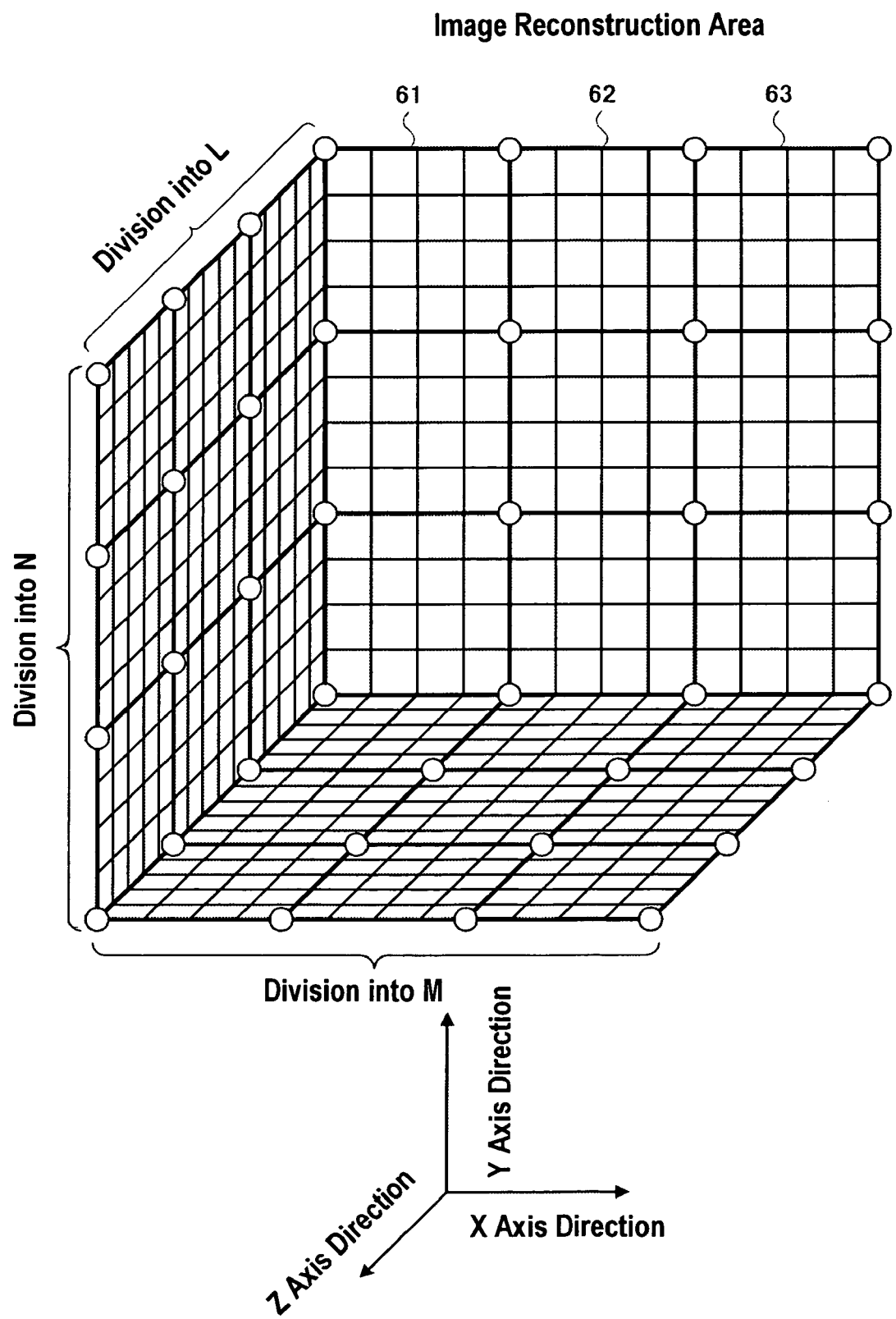
FIG. 5 is a diagram for explaining an example of dividing an image reconstruction area in the tomographic device according to the present invention.

FIG. 5 is a diagram for explaining an example of dividing an image reconstruction area in the tomographic device according to the present invention. In the present embodiment, through a program stored in the central control device 400, 3-dimensional image reconstruction area is divided into image data segments 61~6p of P pieces=M×N×L. When the matrix of image to be reconstructed is 512×512×512, the number of division is determined as follows while assuming the number of division in x axis direction is M, the number of division in y axis direction is N and number of division in z axis direction is L;

M=$2^m$ m is an integer of more than 0
N=$2^n$ n is an integer of more than 0
L=$2^l$ l is an integer of more than 0

By determining the number of division as above, the image reconstruction area can be divided in an equal integer unit size respectively in x, y and z directions, thereby, a processing loop for accessing to respective pixels within the image data segments 6l~6p can be shared in common through out the image data segments 6l~6p, which reduces processing complexity.

Figure 6:
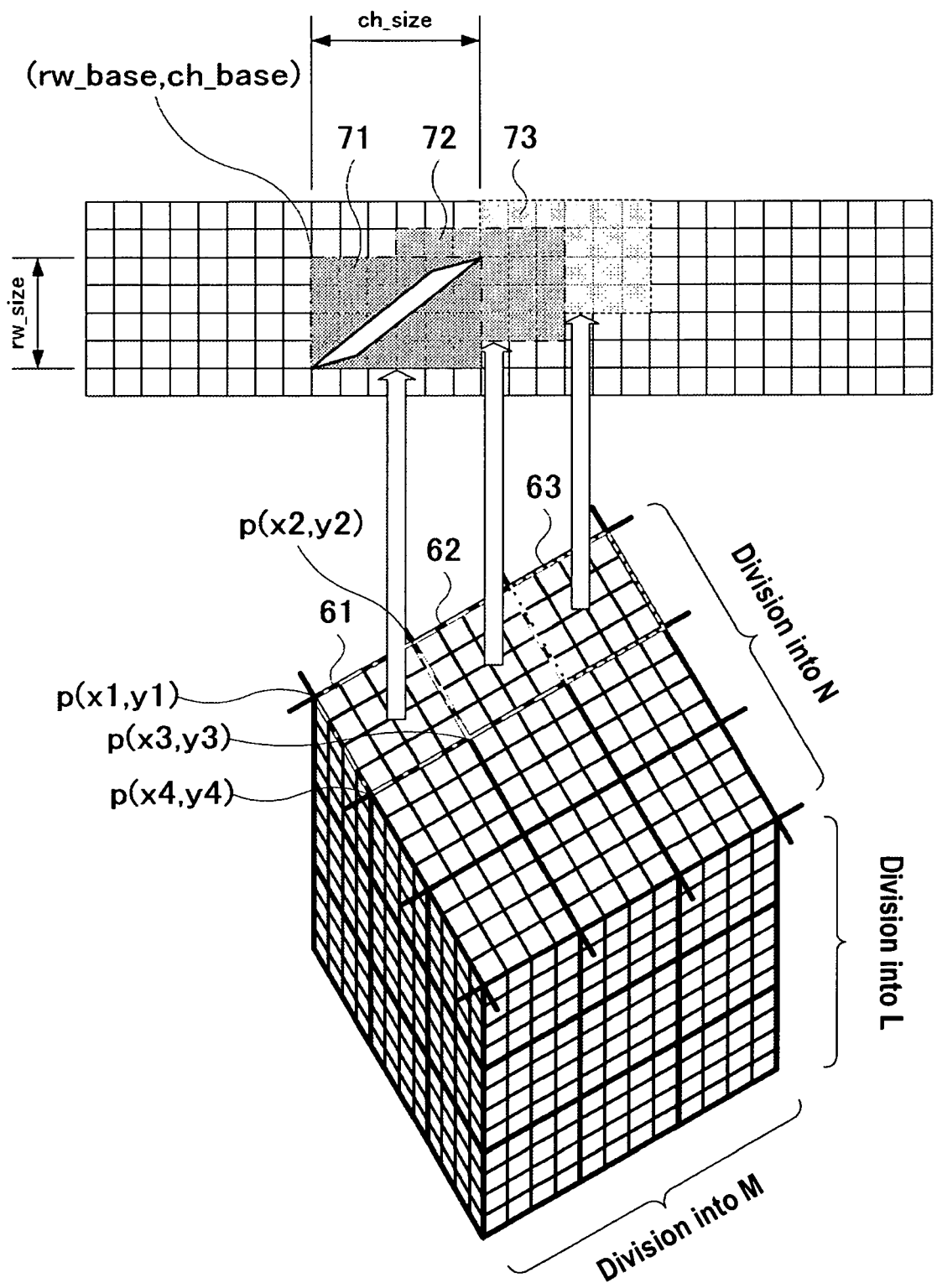
FIG. 6 is a diagram for explaining projection data segments cut out in correspondence with image data segments, which are constituted by dividing the image reconstruction area.

FIG. 6 is a diagram for explaining projection data segments cut out in correspondence with image data segments, which are constituted by dividing the image reconstruction area. In the back projection processing according to an embodiment of the present invention, at first, the projection data input in the computing device 52 are divided and extracted through a programs in the image reconstruction computing device in the computing device 52 into projection data segments 71~73 of small size, which are necessary for reconstructing respective image data segments 61~63 and which are read in and stored in the high speed memory.

Then, through another program stored in the image reconstruction computing device in the computing device 52 the back projection processing is performed based on the projection data segments 71~73 stored in the high speed memory. Further, in this embodiment, for the simplicity's sake, the projection data regions are extracted in a rectangular shape, the regions can be extracted in a form of a polygon such as rhombus and a parallelogram.

Figure 7:
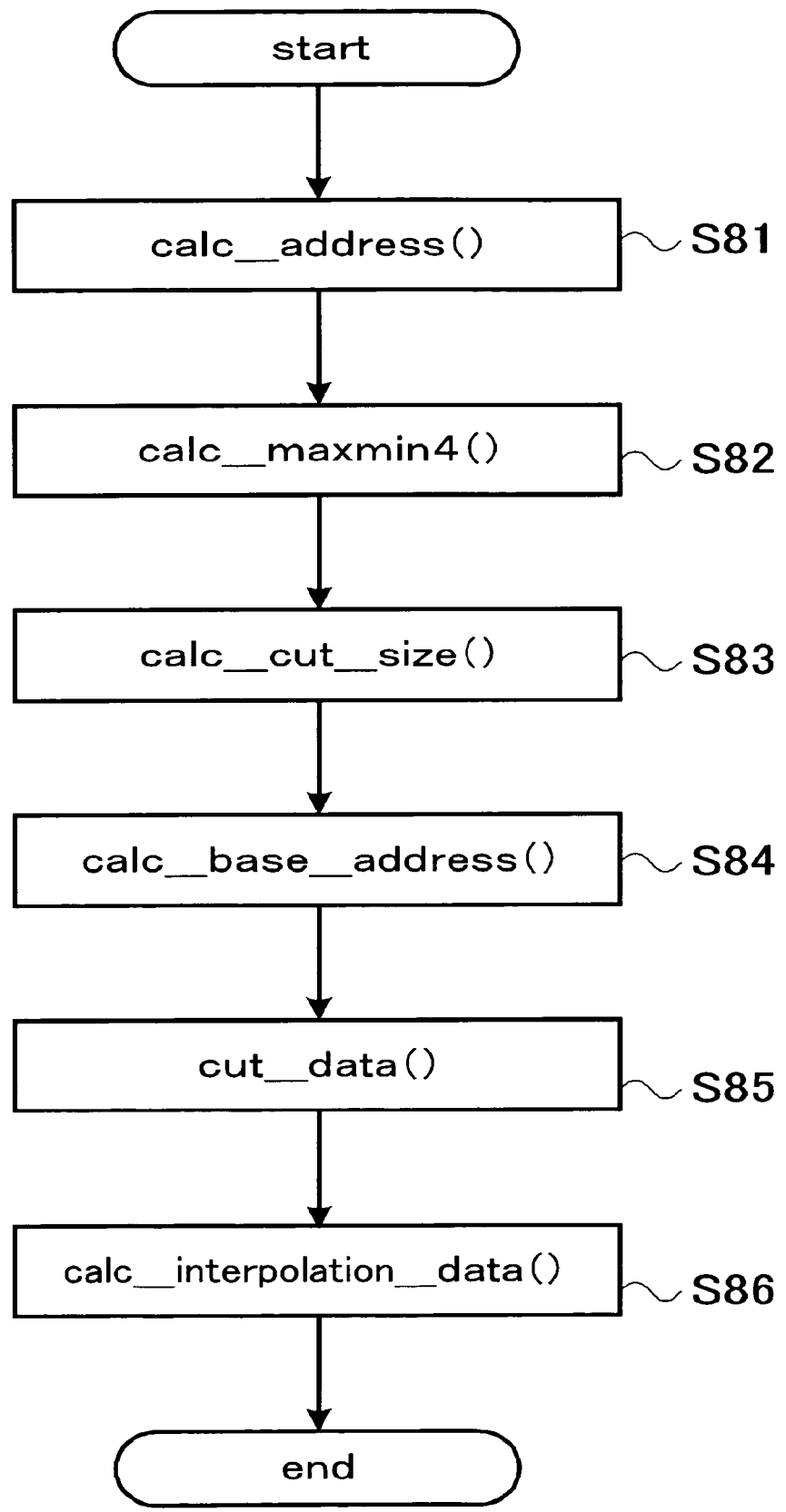
FIG. 7 is a diagram showing a cut out processing flow of the projection data segments corresponding to the image data segments.

FIG. 7 is a diagram showing a cut out processing flow of the projection data segments corresponding to the image data segments. In calc_address ( ) at step S 81, respective detector addresses (rw1,ch1), (rw2,ch2), (rw3,ch3), (rw4,ch4) (addresses on detectors of X-rays passing through four points at corners) of the projection data segment 71 corresponding to the four points at the corner (p(x1,y1),p(x2,y2), p(x3,y3),p(x4,y4)) of the 2-dimensional image data segment 61 are calculated through a program stored in the image reconstruction computing device in the computing device 52. Further, in case of 3-dimensional image data segment, respective detector addresses (rw1,ch1), . . . (rw8,ch8) of the projection data segment corresponding to the eight points at the corner (p(x1,y1,z1),p(x2,y2,z2), . . . p(x8,y8,z8)) are calculated. For the above calculation, the equations (1)~(6) as mentioned above can be used.

In calc_maxmin4 ( ) at step S 82, respective maximum value and minimum value (max_rw,max_ch,min_rw, min_ch) among the four detector addresses calculated at step S 81 are calculated. These values can be calculated by simply comparing the values of the detector addresses (rw1,ch1), (rw2,ch2), (rw3,ch3), (rw4,ch4) . . . .

In calc_cut_size ( ) at step S 83, the sizes (rw_size, ch_size) in the row direction and in the channel direction of the projection data segment 71 as shown in FIG. 6 are calculated based on the detector addresses calculated at step S 82. These sizes can be calculated by substituting the maximum value and minimum value (max_rw,max_ch,min_rw,min_ch) of the detector addresses calculated at step S 82 for the following equations;

rw_size=max_rw−min_rw ch_size=max_ch−min_ch

In calc_base_address ( ) at step S 84, a reference address (rw_base,ch_base) on the projection data of the projection data segment 71 as shown in FIG. 6 is calculated. This address can be calculated by substituting the maximum value and minimum value (max_rw,max_ch,min_rw, min_ch) of the detector addresses calculated at step S 82 for the following equations;

rw_base=min_rw ch_base=min_ch

In cut_data ( ) at step S 85, the projection data segment 71 is extracted from the projection data based on the size (rw_size,ch_size) of the projection data segment 71 and the reference address (rw_base,ch_base). In the present embodiment, although the size of the projection data segment is calculated at step S 83, a predetermined fixed size, which is sufficient for storing the projection data segment, can be used.

Figure 8:
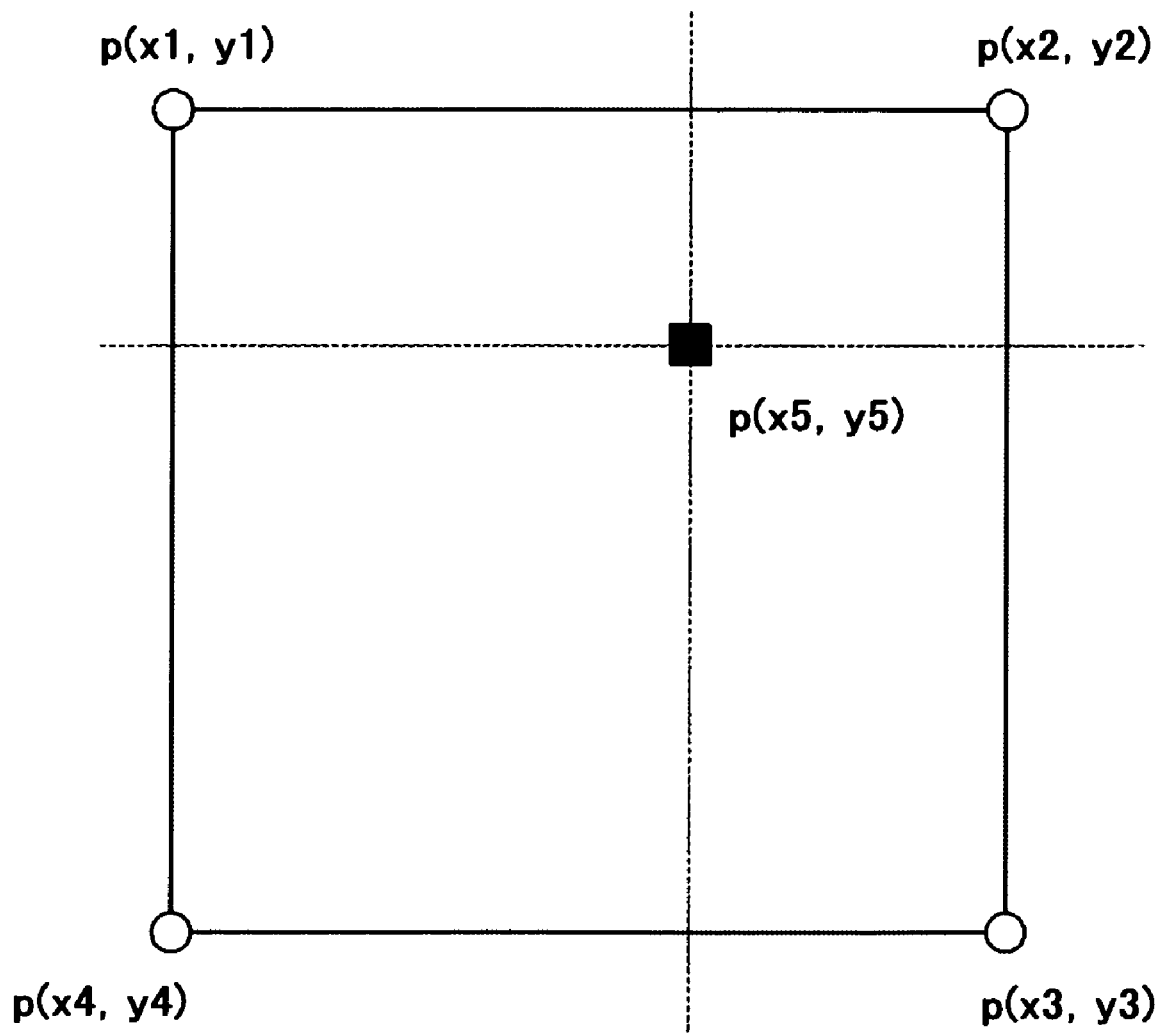
FIG. 8 is a diagram for explaining a general idea of an interpolation processing at step S 86 in FIG. 7.

In calc_interpolation_data ( ) at step S 86, detector addresses at reconstruction points in the image data segment are calculated from a plurality of limited but not all detector addresses in the image data segment 61. FIG. 8 is a diagram for explaining a general idea of an interpolation processing at step S 86. As shown in FIG. 8, through a linear interpolation processing with a program stored in the image reconstruction computing device in the computing device 52 a detector address of a reconstructing pixel point p(x5,y5) is calculated based on the detector addresses corresponding to four corner points p(x1,y1),p(x2,y2),p(x3,y3),p(x4,y4) of the divided image data segment 61 in a rectangle. Specifically, when assuming that the detector addresses corresponding to the four corner points p(x1,y1),p(x2,y2),p(x3,y3),p(x4,y4) as (rw1,ch1),(rw2,ch2),(rw3,ch3),(rw4,ch4), the detector address of the reconstruction point as (rw5,ch5) is determined as follows while multiplying respective interpolation coefficients to the coordinate values and adding the same;

rw5=coeff1*rw1+coeff2*rw2+coeff3*rw3+coeff4*rw4 ch5=coeff1*ch1+coeff2*ch2+coeff3*ch3+coeff4*ch4

Wherein, coeff1,coeff2,coeff3,coeff4 are the interpolation coefficients and in the case of Lagrange interpolation, these are determined as follows;

coeff1=((x5−x2)*(x5−x3)*(x5−x4))/((x1−x2)*(x1−x3)
   *(x1−x4))*((y5−y2)*(y5−y3)*(y5−y4))/((y1−y2)*
   (y1−y3)*(y1−y4))

coeff2=((x5−x1)*(x5−x3)*(x5−x4))/((x2−x1)*(x2−x3)
   *(x2−x4))*((y5−y1)*(y5−y3)*(y5−y4))/((y2−y1)*
   (y2−y3)*(y2−y4))

coeff3=((x5−x1)*(x5−x2)*(x5−x4))/((x3−x1)*(x3−x2)
   *(x3−x4))*((y5−y1)*(y5−y2)*(y5−y4))/((y3−y1)*
   (y3−y2)*(y3−y4))

coeff4=((x5−x1)*(x5−x2)*(x5−x3))/((x4−x1)*(x4−x2)
   *(x4−x3))*((y5−y1)*(y5−y2)*(y5−y3))/((y4−y1)*
   (y4−y2)*(y4−y3))

In this embodiment, although the four corner points are used, the present invention is not limited thereto. Further, a six points interpolation determined from up and down and right and left points can be used. Still further, such detector address calculation through interpolation can be performed only for determining row position of which calculation is complex. After completing the detector address calculation of the reconstruction point in the image data segment 61 at step S 86, like processing is executed for the subsequent image data segment 62 and the projection data segment 72. At this instance, since two points p(x2,y2),p(x3,y3) of the image data segment 61 and the detector addresses (rw2,ch2),(rw3,ch3) of the projection data segment 71 can be shared in common, the processing complexity and memory capacity increase can be reduced. Herein above for the sake of simplifying explanation, the interpolation processing is primarily explained with reference to 2-dimensional image data, like process can be used for 3-dimensional image data.

Herein above, the embodiment of the present invention has been explained in detail, however, such is simply intended for explanation and exemplification and the present invention is not limited thereto.

Further, in the present embodiment, although an example of the tomographic device using X-ray has been explained, the present invention is not limited thereto and the present invention is applicable to a tomographic device using such as neutron beams, positron beams, gamma beams and light beams.

Further, the scanning method of the present invention is not limited to any one of those for the first generation, second generation, third generation and fourth generation and the present invention is applicable to such as a multi tube CT mounting a plurality of X-ray sources, a cathode scanning CT and an electron beam CT. Still further, the present invention can be applicable to a variety of detectors having different configurations such as a detector arranged around a cylindrical surface while disposing an X-ray source at the center, a flat detector, a detector arranged on a spherical surface while disposing an X-ray source at the center and a detector arranged around a cylindrical surface while locating the circumferential revolving axis at the center. Still further, the present invention is not limited to a spiral orbit scan, but can be applicable to a circular orbit scan. Still further, although in the above the image reconstruction area was divided in a same number in x and y directions, the present invention is not limited thereto and the image reconstruction area can be divided in different numbers in x and y directions. Still further, in the above the image reconstruction area was divided in a rectangle in x, y and z space, the image reconstruction area can be divided in a polygon such as a triangle and an octagon, and further, the image reconstruction area can be divided in a polar coordinate.

Still further, with regard to the division of the image data segments to P=M×N×L, the division number can be designed to be input through a provision of a measure which permits such input externally via the input-output device 51. Further, the projection data input to the computing device 52 can be designed displayable through a provision of a measure, which permits the display on the display device in the input-output device 51 together with the divided image data segment regions. More specifically, through connecting the projection data, projection image from front and/or side of a subject being laid down is displayed as scanogram, a 3-dimensional image reconstruction area is set on the scanogram and how the set 3-dimensional image reconstruction area to be divided into the image data segments is designed to be displayable such as by drawing division lines in the 3-dimensional image reconstruction area expressed such as a rectangle and a square. Further, it can be designed that any image data segments can be selectable from the scanogram displayed through a provision of a measure, which permits the selection thereof externally via the input-output device 51.

The invention claimed is:

1. A tomographic device, which comprises a detecting means which is constituted by arranging a plurality of detector elements in 2-dimension and detects X-rays irradiated to a subject and penetrated through the subject, means for producing the detected data as projection data, a projection data memory means which stores the produced projection data, means for dividing an image reconstruction area having a predetermined size corresponding to a region of interest of the subject into image data segment regions having an arbitrary size and an image reconstruction computing means which performs an image reconstruction computing on the divided image data segment regions from the projection data and generates a 3-dimensional tomographic image, wherein the image reconstruction computing means includes extracting means which extracts from the projection data 2-dimensional projection data segment regions corresponding to channel direction and row direction of the detecting means necessary for generating the 3-dimensional tomographic image of the divided image data segment regions, a projection data segment region memory means which stores the extracted 2-dimensional projection data segment regions and a 3 dimensional back projection processing means which successively reads out the 2-dimensional projection data segment regions stored in the projection data segment region memory means and performs 3-dimensional back projection processing for the every respective corresponding image data segment regions.

2. A tomographic device according to claim 1, wherein the processing speed of projection data segment region memory means is higher than that of the projection data memory means.

3. A tomographic device according to claim 2, wherein the extracting means includes means for calculating addresses on the detecting means of the X-rays passing through representative points of the divided image data segment regions based on a predetermined addressing method and means for determining a position on the detecting means of the penetrating rays passing through a point other than the representative points through interpolation based on the calculated positions of the representative points.

4. A tomographic device according to claim 3 wherein the 3-dimensional back projection processing performed by the 3-dimensional back projection processing means is executed by storing successively the data of the extracted 2-dimensional projection data segment regions into the projection data segment region memory means.

5. A tomographic device according to claim 3, wherein the extracting means includes means for calculating addresses on the detecting means of the penetrating rays passing through a plurality of corner points of the divided image data segment regions based on a predetermined addressing method, means for calculating the maximum value and the minimum value in channel direction and row direction among the addresses on the detecting means calculated with regard to the plurality of the corner points, means for calculating size of the 2-dimensional projection data segment regions from the calculated maximum value and minimum value and means for calculating a reference address serving as a reference for the 2-dimensional projection data segment regions from the calculated maximum value and minimum value, and through these means the extraction of the 2-dimensional projection data segment regions is performed.

6. A tomographic device according to claim 1, wherein size and position of the 2-dimensional projection data segment regions to be accessed at the time of back projection to the divided image data segment regions are determined by a plurality of representative points of the divided image data segment regions including 4 or 8 corner points.

7. A tomographic device according to claim 6, wherein addresses of the maximum value and the minimum value of the 2-dimensional projection data segment regions to be accessed at the time of back projection to the divided image data regions are calculated from the plurality of representative points of the divided image data segment regions and the size and positions of the 2-dimensional projection data segment regions are determined by the calculated maximum value and minimum value thereof.

8. A tomographic device according to claim 6, wherein addresses of the 2-dimensional projection data segment regions to be back projected to the divided image data segment regions are calculated through interpolation by making use of addresses of the 2-dimensional projection data segment regions corresponding to the plurality of representative points of the divided image data segment regions.

9. A tomographic device, which comprises a detecting means which is constituted by arranging a plurality of detector elements in 2-dimension and detects X-rays irradiated to a subject and penetrated through the subject, means for producing the detected data as projection data, a projection data memory means which stores the produced projection data, means for dividing an image reconstruction area corresponding to a region of interest of the subject into image data segment regions having an arbitrary size and an image reconstruction computing means which performs an image reconstruction computing on the divided image data segment regions from the projection data and generates a 3-dimensional tomographic image, which further comprises an input means which inputs externally the size of the image reconstruction area to be divided by the dividing means, a display means which displays the projection data together with the position of the divided image data segment regions and a selecting means which selects externally arbitrary image data segment regions from the projection data displayed together with the position of the image data segment regions, wherein the image reconstruction computing means includes an extracting means which extracts from the projection data 2-dimensional projection data segment regions corresponding to channel direction and row direction of the detecting means necessary for generating the 3-dimensional tomographic image of the selected image data segment regions, a projection data segment region memory means which stores the extracted 2-dimensional projection data segment regions and a 3 dimensional back projection processing means which successively reads out the 2dimensional projection data segment regions stored in the projection data segment region memory means and performs 3-dimensional back projection processing for the every respective corresponding image data segment regions.

10. A tomographic method comprising the steps of:
detecting X-rays irradiated to a subject and penetrated through the subject by a detecting means which is constituted by arranging a plurality of detector elements in 2-dimension and producing the detected data as projection data,
storing the produced projection data by a projection data memory means,
dividing an image reconstruction area corresponding to a region of interest of the subject into image data segment regions having an arbitrary size and
performing an image reconstruction computing by an image reconstruction computing means on the divided image data segment regions from the projection data and generating a 3-dimensional tomographic image,
further comprising inputting externally the size of the image reconstruction area to be divided in the dividing step,
displaying die projection data together with the position of the divided image data segment regions,
selecting externally arbitrary image data segment regions from the projection data displayed together with the position of the image data segment regions,
extracting from the projection data 2-dimensional projection data segment regions corresponding to channel direction and row direction of the detecting means necessary for generating the 3-dimensional tomographic image of the selected image data segment regions through the image reconstruction computing means,
storing in a projection data segment region memory means the extracted 2-dimensional projection data segment regions and
performing 3-dimensional back projection processing for the every 2-dimensional projection data segment regions stored in a projection data segment region memory means.

11. A tomographic device, in which penetration rays penetrated through a subject are detected by a detecting means constituted by arranging a plurality of detection elements in 2-dimension, image reconstruction computing is performed by an image reconstruction computing means on an image reconstruction area corresponding to a region of interest of the subject based on the detected projection data and a 3-dimensional tomographic image of the region of interest of the subject is generated, wherein the image reconstruction computing means includes a processing means which divides the image reconstruction area into a plurality of image corresponding to a region of interest of the subject based on the detected projection data and a 3-dimensional tomographic image of the region of interest of the subject is generated, wherein the image reconstruction computing means includes a processing means which divides the image reconstruction area into a plurality of image data segment regions, cuts out from the projection data detected by the detection means 2-dimensional projection data segment regions corresponding to channel direction and row direction of the detecting means necessary for back projecting toward the respective divided image data segment regions and performs a 3-dimensional back projection processing for the every respective corresponding image data segment regions by making use of the data of the respective cut out 2-dimensional projection data segment regions.

12. A tomographic device according to claim 11, the processing means calculates addresses on detecting means of the projection data to be back projected from the respective 2-dimensional projection data segment regions to the respective corresponding image data segment regions according to a predetermined addressing formula for a plurality of representative reconstruction points in the respective image data segment regions and calculates addresses approximately through an interpolation for the remaining reconstruction points based on the calculated addresses on the detecting means of the plurality of the representative reconstruction points.

13. A tomographic device according to claim 11, the 3-dimensional back projection processing performed by the processing means for the respective image data segment regions is performed by storing successively the data of the respective image data segment regions and the data of the corresponding cut out 2-dimensional projection data segment regions in a high speed memory in the image reconstruction computing means.

14. A tomographic device according to claim 11, the cut out of the 2-dimensional projection data segment regions corresponding to the respective image data segment regions by the processing means is performed based on the calculation of the addresses on the detecting means of the projection data corresponding to corner points of the respective image data segment regions based on a predetermined addressing formula, the calculation of the maximum value and the minimum value among the calculated address on the detecting means and the calculation of size of the 2-dimensional projection data segment regions and of a reference address on the projection data segment regions from the calculated maximum value and minimum value of the addresses an the detecting means.

* * * * *